(12) United States Patent
Renger

(10) Patent No.: US 6,178,079 B1
(45) Date of Patent: Jan. 23, 2001

(54) MAGNETIC ANNUNCIATOR

(75) Inventor: Herman Lee Renger, Calabasas, CA (US)

(73) Assignee: Pacesetter, Inc., Sylmar, CA (US)

( * ) Notice: Under 35 U.S.C. 154(b), the term of this patent shall be extended for 0 days.

(21) Appl. No.: 08/648,848

(22) Filed: May 16, 1996

(51) Int. Cl.[7] ..................................... H02H 1/00
(52) U.S. Cl. ............................. 361/118; 361/115
(58) Field of Search .................................. 361/118, 115; 323/282; 307/80; 335/222

(56) References Cited

U.S. PATENT DOCUMENTS

| | | | |
|---|---|---|---|
| 3,783,877 | 1/1974 | Bowers | 128/419 P |
| 4,086,916 | 5/1978 | Freeman et al. | 128/2.05 T |
| 4,088,139 | 5/1978 | Auerbach | 128/419 PT |
| 4,102,346 | 7/1978 | Fulker | 128/419 PS |
| 4,210,149 | 7/1980 | Heilman et al. | 128/419 D |
| 4,295,474 | 10/1981 | Fischell | 128/697 |
| 4,345,603 | 8/1982 | Schulman | 128/419 PT |
| 4,407,289 | 10/1983 | Nappholz et al. | 128/419 PG |
| 5,036,239 | * 7/1991 | Yamaguchi | 310/268 |
| 5,190,034 | 3/1993 | Sholder | 128/419 PG |
| 5,745,019 | * 4/1998 | Renger | 335/222 |

* cited by examiner

Primary Examiner—Stephen W. Jackson

(57) ABSTRACT

An annunciator for an organ stimulating system implantable in the body of a person comprises a hollow canister having a cylindrical internal cavity, first and second electrically conductive coils encircling the canister lying in transverse, preferably perpendicular, planes which intersect along the longitudinal axis of the internal cavity, and a cylindrical permanent magnetic roller having an outer peripheral surface engageable with an inner peripheral surface of the canister and being freely rotatable within the canister. The roller is magnetized at right angles to the roller axis producing a permanent magnetic field and signal generators, either AC or DC, sequentially energize the electrically conductive coils to produce a rotating magnetic field interacting with the permanent magnetic field of the roller and causing the roller to roll about the inner peripheral surface of the canister. The permanent magnetic roller, by its movement, produces vibrations which are imparted to the casing of the organ stimulating system. Specifically, the rolling motion of the roller results in a movement of its center of gravity in a vibration producing orbit. The orbital frequency, $\Omega$, of the center of gravity of the roller is b $\omega \cdot d/(D-d)$, where $\omega$=rate of rotation of said roller, d=diameter of said roller, and D=inner diameter of the cavity of said canister. In another embodiment, the roller may be replaced by a ball and the internal cavity may be spherical or ellipsoidal.

31 Claims, 7 Drawing Sheets

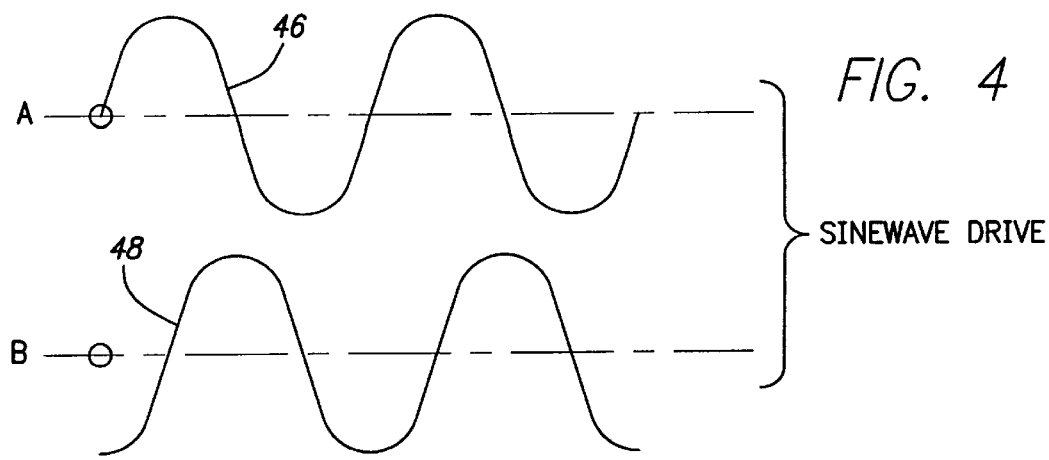
FIG. 4 — SINEWAVE DRIVE
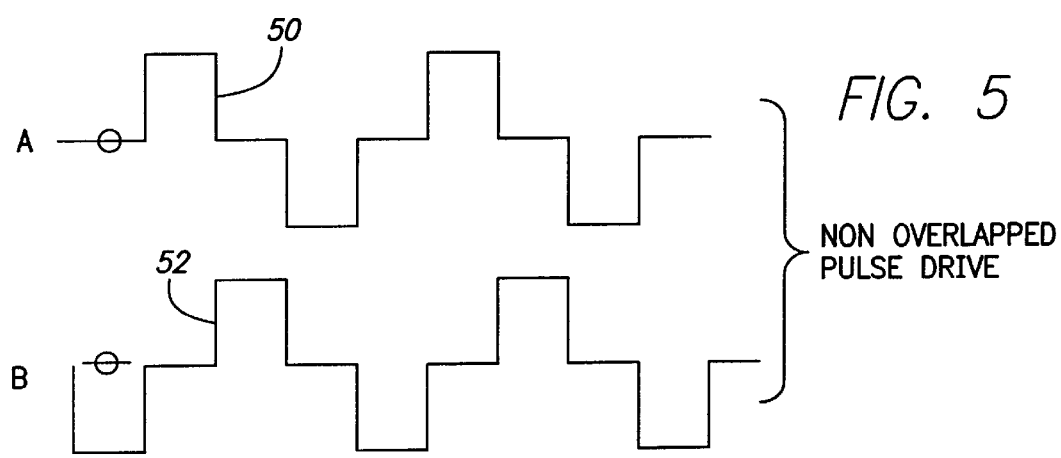
FIG. 5 — NON OVERLAPPED PULSE DRIVE
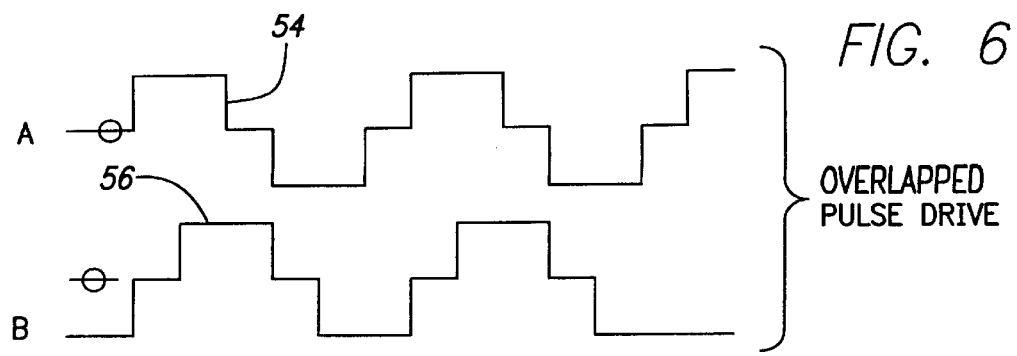
FIG. 6 — OVERLAPPED PULSE DRIVE

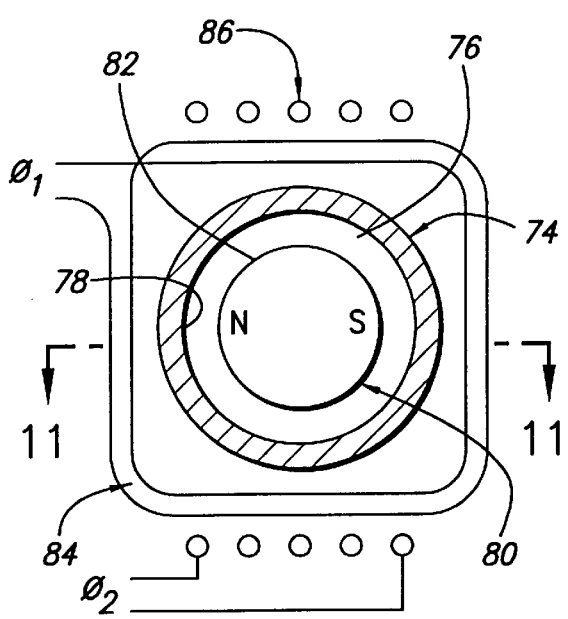
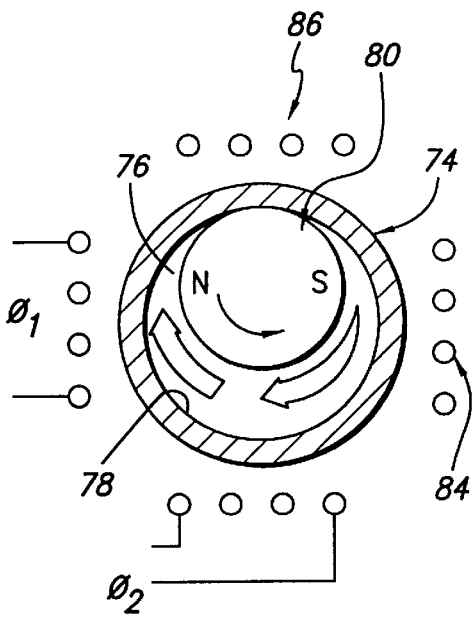
FIG. 10   FIG. 11
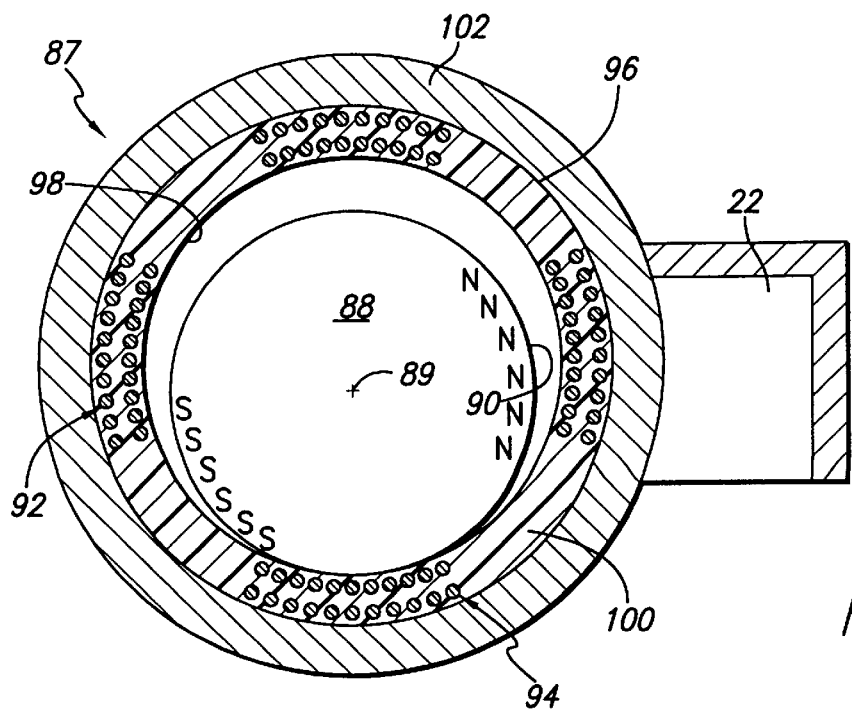
FIG. 12

MAGNETIC ANNUNCIATOR

FIELD OF THE INVENTION

The present invention relates to annunciator devices for organ stimulating systems implantable in the body of a patient and in particular to such devices which may be used in combination with implantable defibrillator systems, for example, and be assured of attracting the attention of the patient upon the occurrence of a predetermined event.

BACKGROUND OF THE INVENTION

Implantable defibrillation systems are known in the art which deliver a high-voltage defibrillation pulse to the heart when the onset of fibrillation is detected and/or in the event of a detected complete loss of cardiac output. Such known devices are also capable, if the heart exhibits an arrhythmia such as atrial fibrillation, atrial flutter or tachycardia, or ventricular tachycardia, of cardioverting the heart by delivering a low-voltage pulse in an attempt to regain synchronous operation of the heart, instead of delivering the high voltage defibrillation pulse. In known devices of this type, it would be desirable to provide a compact, efficient device to alert the patient that his implanted device needs attention or is about to defibrillate.

It is known from U.S. Pat. No. 4,086,916 to Freeman at al., for example, to contain a cardiac monitoring system in a wristwatch worn by a patient, the system including circuitry for detecting an erratic heartbeat, a missing pulse or other irregularities and providing an alarm indication, audio and visual, when such an event is detected.

An implantable pacing system is disclosed in U.S. Pat. No. 4,102,346 to Fulker which includes an alarm device as part of the implanted unit which generates an alarm signal to inform the pacemaker user when the battery source of power of the pacemaker is nearing end of life or is malfunctioning.

An implantable tissue stimulating device is disclosed in U.S. Pat. No. 4,345,603 to Schulman which activates an alarm which informs the patient in whom the system is implanted that the battery is in need of replacement. After the user has been so informed, the user applies a magnet externally in the vicinity of the implanted unit to deactivate the monitoring system and thereby cease the continued operation of the alarm.

A pacemaker for controlling tachycardia is disclosed in U.S. Pat. No. 4,407,289 to Nappholz et al. also disclosing means for informing a pacemaker user of the remaining battery life. The user places a magnet externally in the vicinity of the implanted unit, which thereby causes the implanted unit to generate two pulses which can be seen on the patient's ECG waveform. The time separation between the two pulses indicates the remaining battery potential. Application of the magnet, after the pulses have been generated, temporarily disables the device.

In U.S. Pat. No. 5,190,034 to Sholder, an implantable arrhythmia treatment system is disclosed which includes reliable protection against the release of unneeded treatment pulses, that is, which provides protection against a false-positive output. The disclosed system utilizes an alarm generator which may be disposed in the implanted unit, or in an external unit. The alarm may be of any type which does not require constant, active monitoring by the user, such as a sensory alarm, for example, an audio alarm generator or a tactile alarm generator or "tickler".

Other examples of implantable arrhythmia devices which include an alarm generator, either audio, tactile, or visual, are found in U.S. Pat. Nos. 4,295,474 to Fischell; 4,210,149 to Heilman et al.; and 3,783,877 to Bowers.

According to the current state of the art, error conditions are typically announced within an implantable cardioverter defibrillator (ICD) using a piezo annunciator or beeper. The current Eagle Model 2800 in development by Pacesetter, Inc., A St. Jude Medical Company of Sylmar, Calif., for example, utilizes a piezo actuator to flex the titanium can at audio frequencies. However, in some instances, the efficacy of audio emissions from devices implanted abdominally can be questioned. The attenuation of the audio transmitted through tissue is dramatic and aged patients commonly have hearing loss that further decreases their sensitivity to implanted audio generators.

It was in light of the foregoing that the present invention was conceived and has now been reduced to practice.

SUMMARY OF THE INVENTION

According to the invention, an annunciator is provided for an organ stimulating system which is implantable in the body of a patient. In one embodiment, it comprises a hollow canister having a cylindrical internal cavity, first and second electrically conductive coils encircling the canister lying in transverse, preferably perpendicular, planes which intersect along the longitudinal axis of the internal cavity, and a cylindrical permanent magnetic roller having an outer peripheral surface engageable with an inner peripheral surface of the canister and being freely rotatable within the canister. The roller is magnetized at right angles to the roller axis producing a permanent magnetic field and signal generators, either AC or DC, sequentially energize the electrically conductive coils to produce a rotating magnetic field interacting with the permanent magnetic field of the roller and causing the roller to roll about the inner peripheral surface of the canister. The permanent magnetic roller, by its movement, produces vibrations which are imparted to the casing of the organ stimulating system. Specifically, the rolling motion of the roller results in a movement of its center of gravity in a vibration producing orbit. The orbital frequency, $\Omega$, of the center of gravity of the roller is $\omega \cdot d/(D-d)$, where $\omega$=rate of rotation of said roller, d=diameter of said roller, and D=inner diameter of the cavity of said canister. In another embodiment, the roller may be replaced by a ball and the internal cavity may be spherical or ellipsoidal.

A primary object of the invention, therefore, is to produce an annunciator for an implanted pacemaker which produces vibration, has low power requirements, and requires minimal space.

In another manner of describing the invention, a magnetized ball or cylinder is placed between two or more coils in a cylindrical cavity or other appropriately shaped cavity. When the coils are driven appropriately, either at a fixed frequency, at an externally derived variable frequency, or as triggered pulses dependent on voltages induced in the coils by the motion of the magnet, the magnetized element is caused to roll around inside the cavity and produce vibrations. In the case of the cylindrical magnet additional non magnetic balls can be placed between the ends of the magnet and the ends of the cavity to act as bearings and coincidentally produce additional vibration at a frequency different from that of the magnet. Where the current pulses to the coils are triggered by voltages induced in the coils the unit is acting as a brushless motor. If higher frequency vibrations are desired, ridges can be formed on either the magnet or the cavity. Either pulsed DC or AC may be employed to drive the invention.

The present invention offers numerous advantages. It provides a novel annunciator device applicable to organ stimulating systems which are implantable in a patient's body. More particularly, the invention may be used in combination with implantable defibrillator systems, for example, and be assured of attracting the attention of the patient upon the occurrence of a predetermined event. Still more particularly, the invention may serve to produce a subaudible vibration which would be detectible by a patient who may have experienced hearing loss. The invention assures a compact structure of simplified design fabricated from commonly available materials and requiring expenditure of minimal electrical energy.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIGS. 4A and 4B are graphs depicting AC signals imparted, respectively, by each of the signal generators illustrated in FIG. 1;

FIGS. 5A and 5B are graphs depicting non-overlapped DC-pulsed signals imparted, respectively, by each of the signal generators illustrated in FIG. 1;

FIGS. 6A and 6B are graphs depicting overlapped DC-pulsed signals imparted, respectively, by each of the signal generators illustrated in FIG. 1;

FIG. 10 is a diagrammatic cross section view, similar to FIG. 2, but illustrating another embodiment of the invention;

FIG. 11 is a diagrammatic cross section view taken generally along line 11—11 in FIG. 10;

FIG. 12 is a diagrammatic transverse cross section view illustrating another modified annunciator of the invention;

DESCRIPTION OF THE PREFERRED EMBODIMENTS

Figure 1:
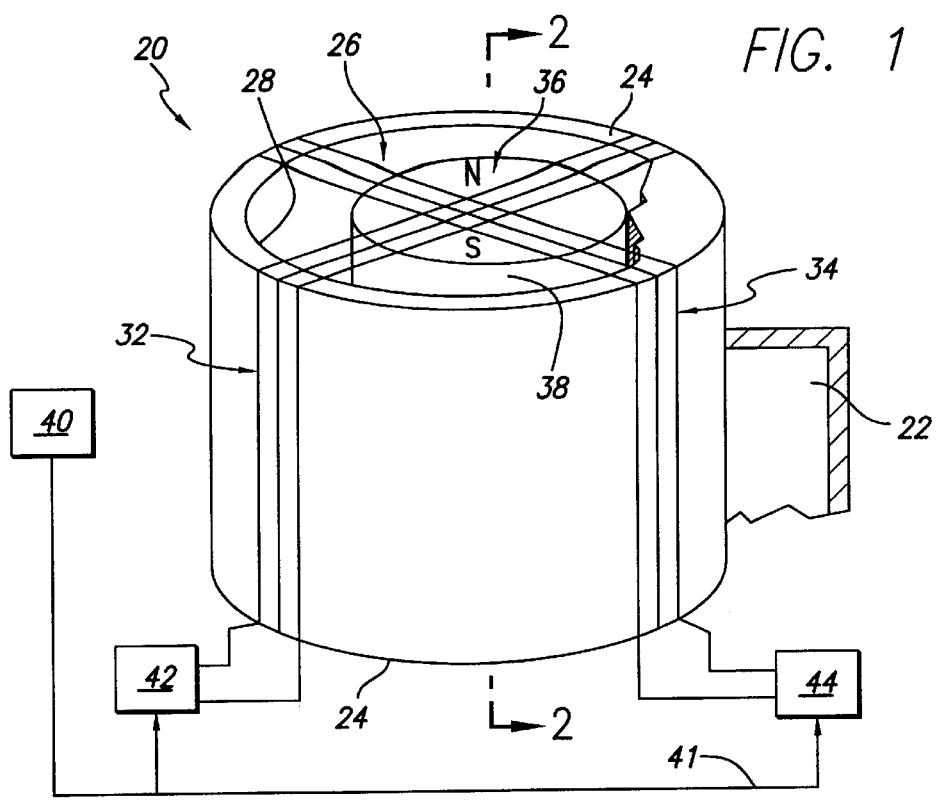
FIG. 1 is a diagrammatic view, partly in perspective and partly broken away and in section, of an annunciator, embodying the present invention, for an organ stimulating system implantable in the body of a patient.
Figure 2:
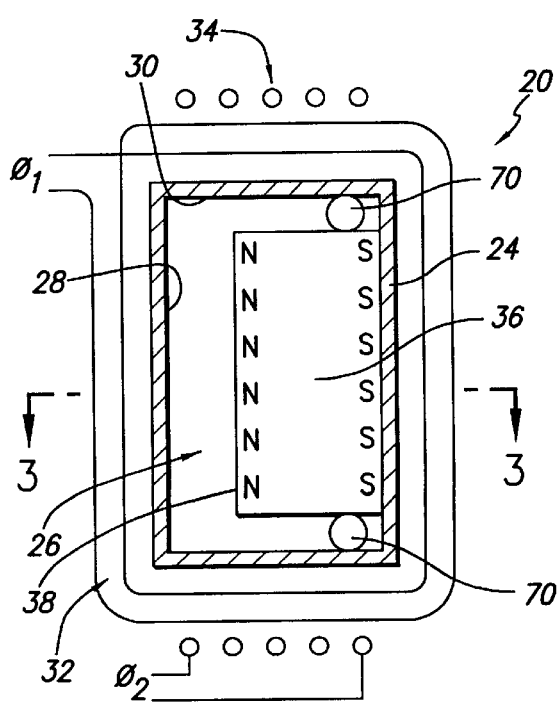
FIG. 2 is a diagrammatic cross section view taken generally along line 2—2 in FIG. 1.
Figure 3:
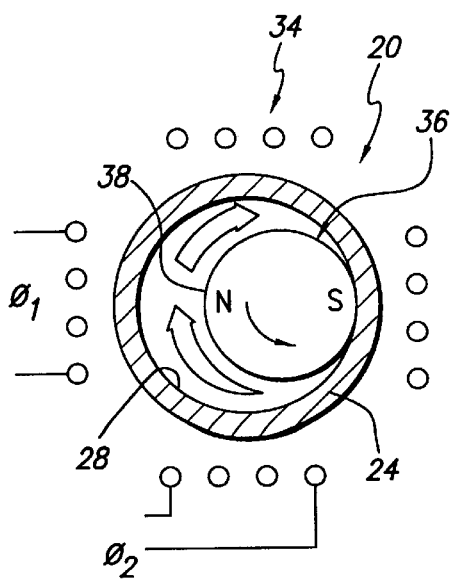
FIG. 3 is a diagrammatic cross section view taken generally along line 3—3 in FIG. 2.
Figure 7A:
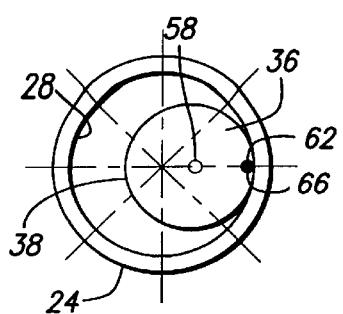
FIGS. 7A through 7I are a series of diagrammatic transverse cross section views of a canister, one of the components illustrated in FIG. 1, illustrating a plurality of successive positions of a magnetic roller therein.
Figure 7B:
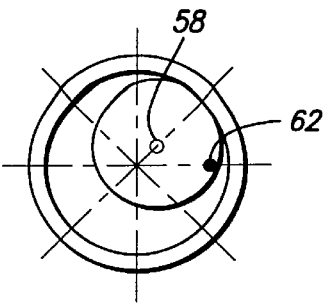
Figure 7C:
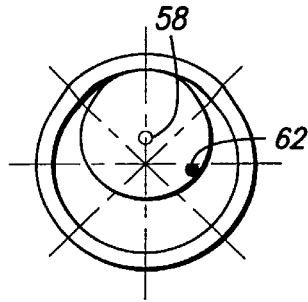
Figure 7D:
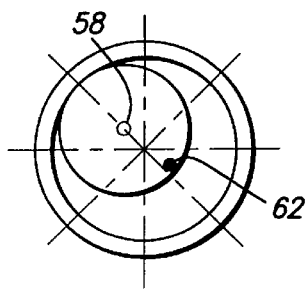
Figure 7E:
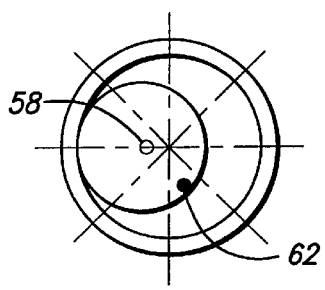
Figure 7F:
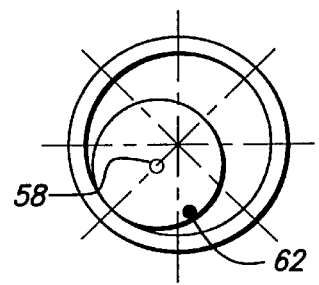
Figure 7G:
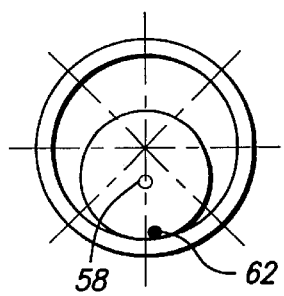
Figure 7H:
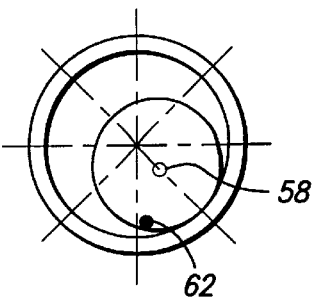
Figure 7I:
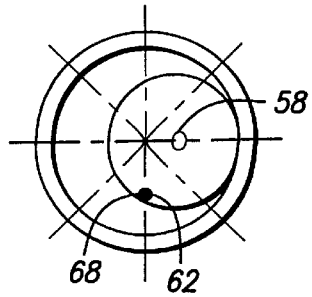

Turn now to the drawings and, initially, to FIGS. 1–3 which diagrammatically illustrate an annunciator 20 embodying the present invention encapsulated within a casing 22 for an organ stimulating system. The annunciator 20 comprises a canister 24 mounted on the casing 22 and has a cylindrical internal cavity 26 defined by an inner peripheral surface 28, and opposed inner terminal surfaces 30.

A first electrically conductive coil 32 encircles the canister 24 and lies generally in a plane of the longitudinal axis of the internal cavity 26. A second electrically conductive coil 34 similarly encircles the canister 24, lies in a plane transverse to the plane of the first conductive coil, and intersects the coil 32 along the longitudinal axis of the internal cavity 26.

A cylindrical permanent magnetic roller 36 is rotatable about a longitudinally extending roller axis and has an outer peripheral surface 38 engageable with the inner peripheral surface 28 of the canister. The roller 36 is freely rotatable within the internal cavity 26 and is magnetized at right angles to the roller axis to produce a permanent magnetic field. The magnetization of the roller 36 is indicated in the drawings by the notations "N" and "S" indicating north polarity and south polarity, respectively.

Pacemaker circuitry is diagrammatically indicated at 40 in FIG. 1 and is taken to include a battery or other suitable source of EMF for sequentially energizing the first and second coils 32, 34, via enable line 41 and signal generators 42, 44, respectively, to produce a rotating magnetic field interacting with the permanent magnetic field of the magnetic roller 36. With the coils 32, 34 thereby energized, the magnetic roller 36 is caused to roll about the internal cavity 26, engaged with the inner peripheral surface 28. As it rotates, rolling on the inner peripheral surface 28, the permanent magnetic roller 36 produces vibrations which are imparted to the casing 22 of the organ stimulating system.

The signal generators 42, 44 serve to apply a periodic current to the first and second electrically conductive coils 32, 34, respectively. In one instance, as seen in FIG. 4A, an AC cyclic, sine wave, signal 46 may be imparted by the signal generator 42 to the coil 32 while a cyclic, sine wave, signal 48 may be imparted by the signal generator 44 to the coil 34. The signal 48 is preferably 90° out of phase relative to the signal 46 in order to assure uniform and optimum driving force imparted to the magnetic roller 36.

In another instance, as seen in FIG. 5A, a DC pulse signal 50 may be imparted by the signal generator 42 to the coil 32 while a DC pulse signal 52 may be imparted by the signal generator 44 to the coil 34. As with the FIG. 4 mode of operation, the signal 52 is preferably out of phase relative to the signal 46 and offset in order to assure a uniform and optimum driving force imparted to the magnetic roller 36.

In still another instance, as seen in FIG. 6A, the DC pulse signals 50, 52 imparted by the signal generators 42, 44 to the coils 32, 34 may be overlapped and the resulting overlapped signals 54, 56 offset, again to assure a uniform and optimum driving force imparted to the magnetic roller 36.

As seen in FIGS. 7A–7I, the permanent magnetic roller 36 for the annunciator of the invention has a center of gravity indicated at 58. The rolling motion of the permanent magnetic roller 36 about the internal cavity 26 of the canister 24 on the inner peripheral surface 28 results in a movement of the center of gravity in an orbit which produces the vibrations which are imparted to the casing 22 of the organ stimulating system. It will be seen that an imaginary point 62 on the magnetic roller 36 advances along an arcuate path and that during the time of completion for one revolution by the center of gravity 58, the imaginary point only advances from a location 66 on the internal cavity to a location 68 thereon. As a result, it is clear that the rotational speed, or frequency, of the center of gravity of the roller 36 is much greater than that of the roller itself. The orbital frequency, $\Omega$, of said center of gravity of the permanent magnetic roller is $\omega \cdot d/(D-d)$ where $\omega$=rate of rotation of the roller, where d=diameter of the roller, and where D=inner diameter of the cavity of the canister. In actual fact, the vibrations imparted to the casing of the organ stimulating system exhibit a frequency exceeding both the rate of rotation of the magnetic roller about the roller axis and the rate of the sequential energization of the first and second coils.

For optimum results, again to assure a uniform and optimum driving force being imparted to the magnetic roller 36, it is preferred that the second conductive coil 34 lies in a plane perpendicular to that of the first conductive coil 32.

In the operation of the annunciator 20, the motion of the magnetic roller 36 within the coils 32, 34 will induce voltages which can be used to trigger drive pulses 46, 48 or 50, 52 or 54, 56. FIGS. 4, 5, and 6 show the time relationships for these drive pulses. In each instance, the frequency of vibration will be higher than the rotational rate of the magnetic roller 36 or the coil pulse frequency. This relationship is:

$$\Omega = W \frac{d}{D-d}$$

where $\Omega$=the orbital frequency of the magnet's center of gravity, also the vibration frequency.
W=rotation rate of magnet, also pulse frequency
d=magnet diameter
D=cavity diameter.
As the magnitude of d approaches that of D, the value of $\Omega$ becomes very large. The unbalanced centrifugal force thereby generated can be expressed as:

$$F = M \frac{\Omega^2}{(D-d)} = M \frac{W^2 d^2}{(D-d)^3}.$$

Again the force value becomes very large as d approaches D.

Figure 8:
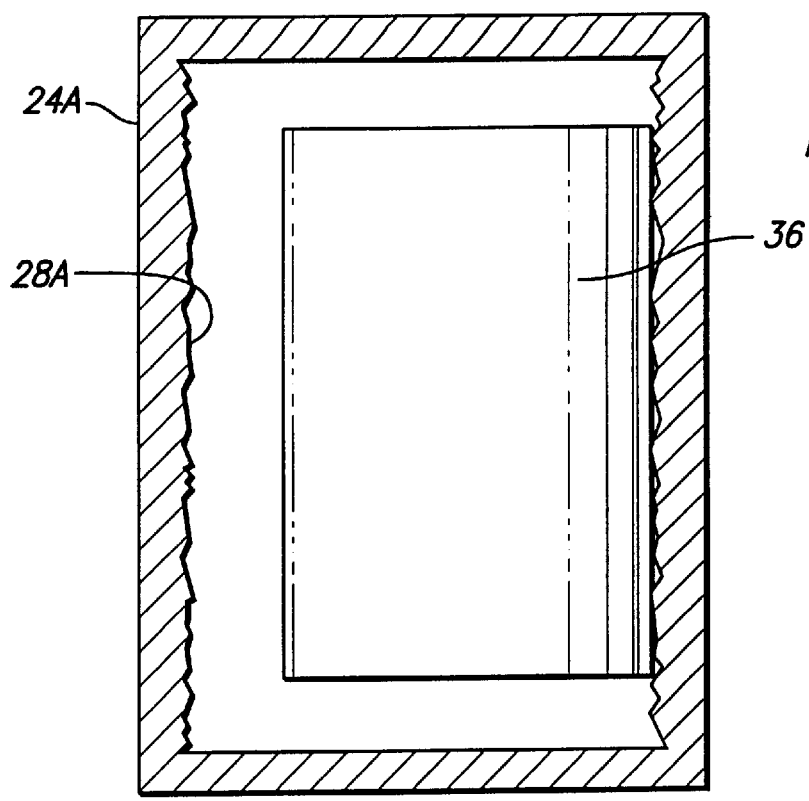
FIG. 8 is a longitudinal cross section view of a modified canister of the invention, similar to the view of the canister depicted in FIG. 2, to illustrate another embodiment of the invention.

As seen in FIG. 8, a modified canister 24A is provided in order to assure optimum traction of the permanent magnetic roller on the inner peripheral surface 28A thereof. The surface 28A has been roughened in any suitable manner and it will be understood that it would be equivalent to roughen the outer peripheral surface of the roller instead.

Yet another embodiment of the invention is illustrated in FIG. 2 which illustrates a plurality of non-magnetic miniballs 70 within the internal cavity of the canister and interposed between the ends of the permanent magnetic roller 36 and the inner terminal surfaces 30 for minimizing friction therebetween.

Figure 9:
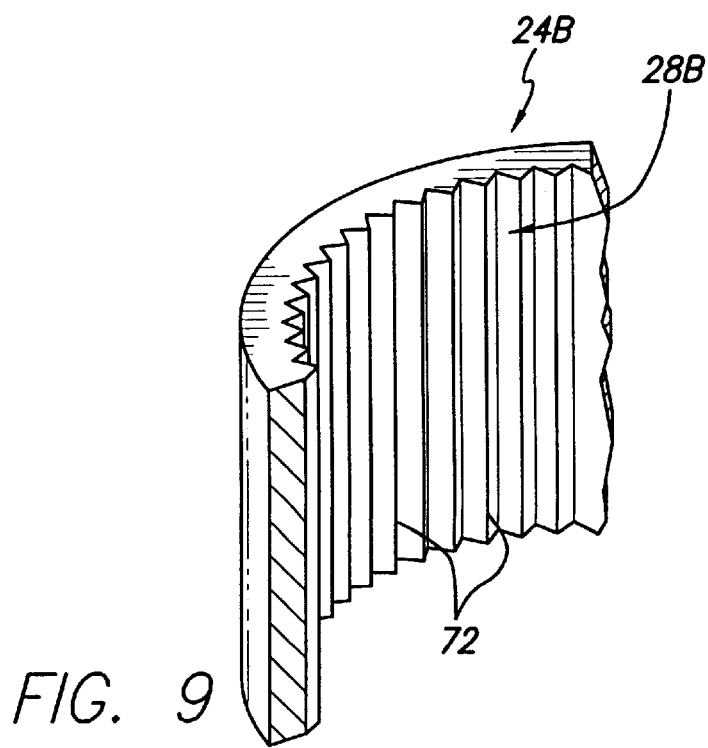
FIG. 9 is a detail perspective view diagrammatically illustrating another embodiment of the invention.

In FIG. 9, still another embodiment is depicted in which a modified inner peripheral surface 28B of a canister 24B is formed with a plurality of parallel, spaced, longitudinally extending ridges 72 for producing additional vibrations as the permanent magnetic roller 36 rolls therealong. It will be understood that it would be equivalent to form the outer peripheral surface of the roller instead with a plurality of parallel, spaced, longitudinally extending ridges (not shown) for producing additional vibrations as the permanent magnetic roller 36 rolls along the inner peripheral surface of the canister.

Yet another embodiment of the invention is illustrated in FIGS. 10 and 11. In this instance, a modified canister 74 has an internal cavity 76 with an inner peripheral surface 78 which may be spherical shaped, ellipsoidal shaped or of some other suitable continuous, smoothly contoured, shape. A permanent magnetic spherical ball 80 has an outer peripheral surface 82 engageable with the inner peripheral surface 78 of the canister and is freely rotatable within the internal cavity thereof. The permanent magnetic ball 80 is magnetized along a major diameter, as indicated by the respective notations "N" and "S", and produces a magnetic field. As in the embodiment of FIGS. 1–3, first and second coils 84, 86 are sequentially energized to produce a rotating magnetic field interacting with the permanent magnetic field of the magnetic ball to thereby cause the magnetic ball to roll about the internal cavity of the canister 74 engaged with the inner peripheral surface 78. In this instance, as with the roller 36, the permanent magnetic ball 80, by its movement, produces vibrations which are imparted to the casing of the organ stimulating system.

In the instance that the internal cavity is spherical in shape, the planes of the coils 84, 86 intersect at the center of the cavity 76. In the instance that the internal cavity is ellipsoidal in shape, the conductive coils may intersect, in one instance, along a longitudinal, or major, axis of the internal cavity of the canister and, in another instance, along a lateral, or minor, axis of the internal cavity of the canister.

Still another embodiment of the invention is illustrated in FIG. 12. In this instance, a modified annunciator 87 includes a cylindrical permanent magnetic roller 88 which is rotatable about a longitudinally extending roller axis 89 and has an outer peripheral surface 90. The magnetic roller. 88 is magnetized at right angles to the roller axis, as indicated by the respective notations "N" and "S", to thereby produce a permanent magnetic field. A first electrically conductive coil 92 encircles the permanent magnetic roller 88 and lies generally in a first plane. A second electrically conductive coil 94 also encircles the permanent magnetic roller and lies in a second plane transverse to the plane of the first conductive coil.

The electrically conductive coils 92, 94 are mounted on the casing 22 for the organ stimulating system in a suitable manner and together define a generally cylindrical internal cavity defined by an inner peripheral surface 98. The annunciator 87 also includes opposed inner terminal surfaces which are not illustrated but are provided in the manner of the opposed inner terminal surfaces 30 of the annunciator 20 (FIG. 2). The first and second electrically conductive coils 92, 94 intersect along the longitudinal axis of the internal cavity 96 and the permanent magnetic roller 88 is engageable with the inner peripheral surface 98 and is freely rotatable within the internal cavity.

Although it is acceptable for purposes of the invention for the permanent magnetic roller 88 to roll in engagement with the bare wires of the electrically conductive coils 92, 94, it is preferred to provide a plastic protective sheath 100 of polymeric or other suitable non-conductive material to encapsulate the coils. It is also preferred, although not necessary, to provide a housing 102 of iron or other suitable magnetically permeable material surrounding the plastic sheath to enhance the operation of the annunciator.

Similarly, it is desirable for the improved operation of the annunciator 87 if the first and second coils 92, 94 are positioned in mutually perpendicular planes.

As with the earlier described embodiments of the invention, in the annunciator 87, the first and second coils 92, 94 are sequentially energized to produce a rotating magnetic field which interacts with the permanent magnetic field of the magnetic roller 88 to thereby cause the magnetic roller to roll about the internal cavity 96 engaged with the inner peripheral surface 98. The movement of the permanent magnetic roller produces vibrations which are imparted to the casing 22 of the organ stimulating system. Also, as in the earlier described embodiments, a spherical ball (not. shown) is considered to be equivalent to the roller 88.

Figure 13:
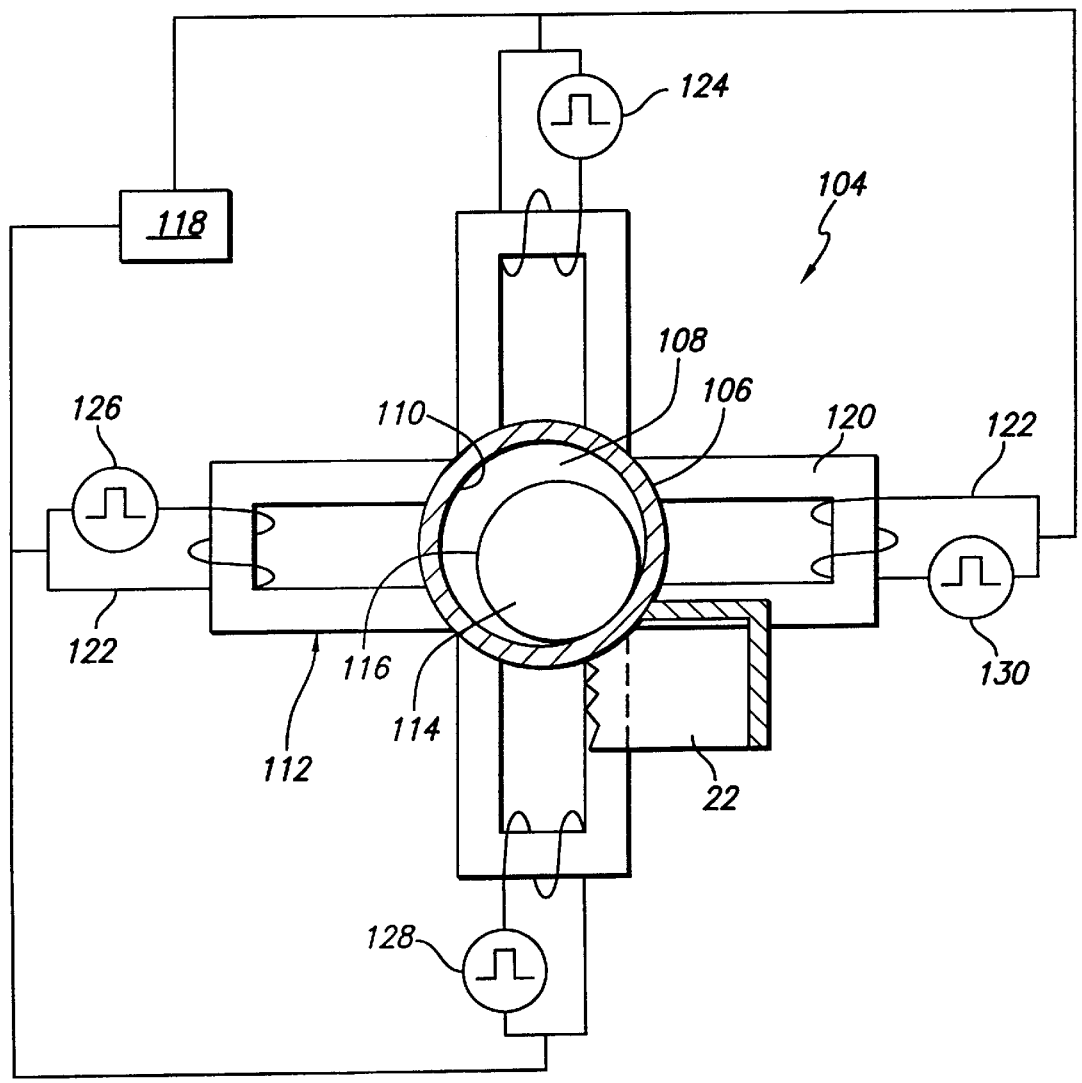
FIG. 13 is a diagrammatic view, partially cut away and in section, of still another embodiment of the invention.
Figure 14:
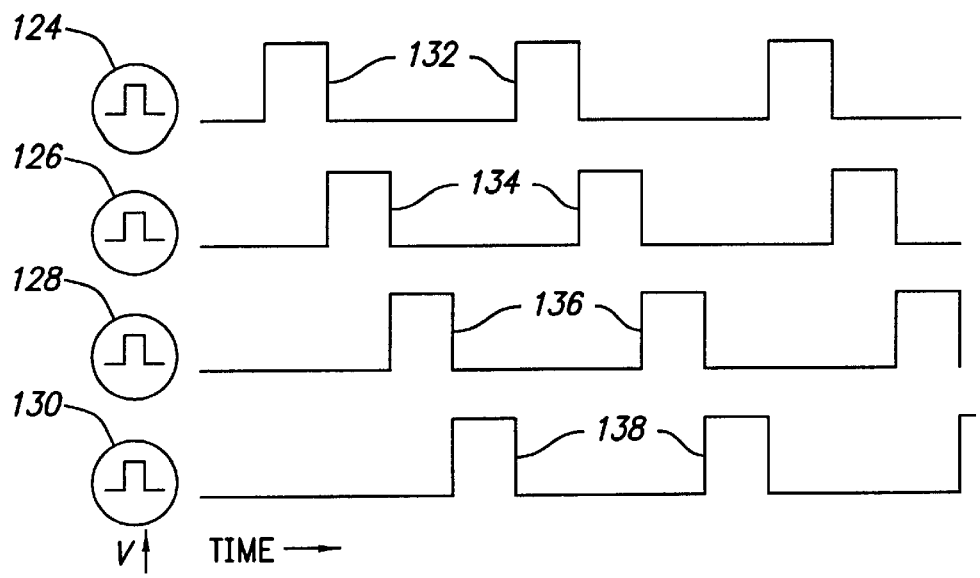
FIGS. 14A, 14B, 14C, and 14D are graphs depicting a plurality of sequential DC-pulsed signals imparted, respectively, by each of the signal generators illustrated in FIG. 13.
Figure 15:
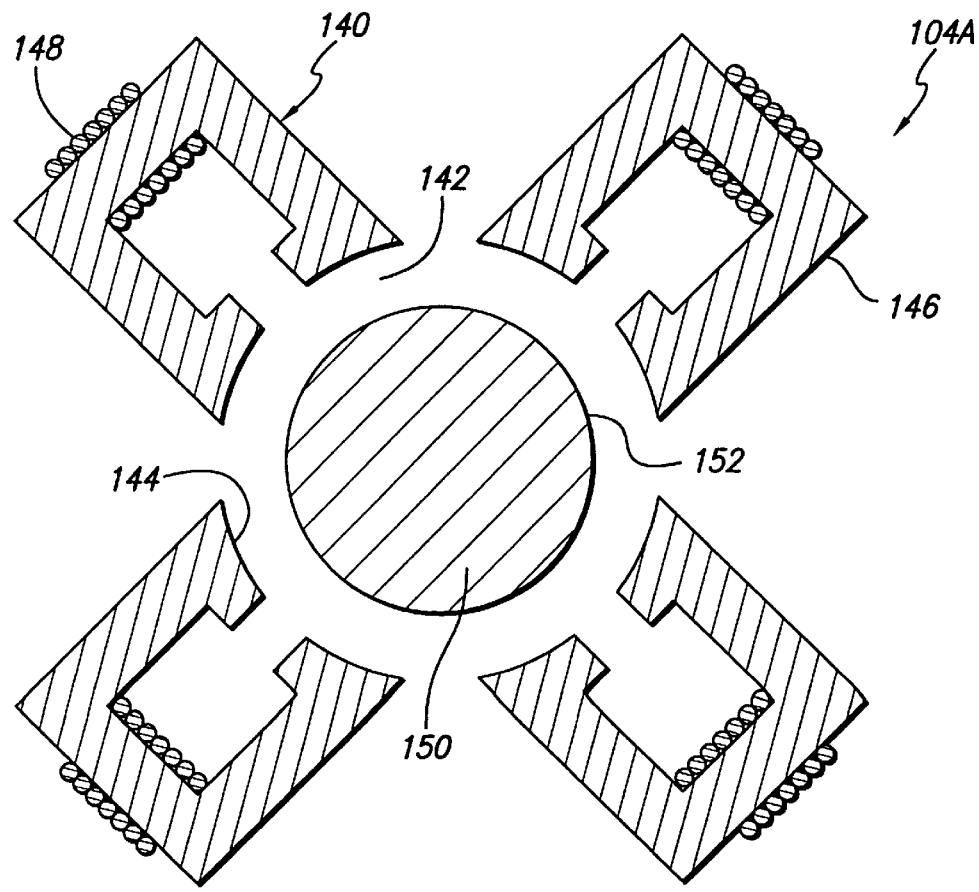
FIG. 15 is a diagrammatic view of another modification of the embodiment of FIG. 13.

Still a further embodiment of the invention will now be disclosed with the aid of FIGS. 13, 14, and 15. In this instance, an annunciator 104 includes a canister 106 mounted on the casing 22 of the organ stimulating system. The canister 106 has a cylindrical internal cavity 108 with an inner peripheral surface 110. A plurality of electromagnets 112 are attached to the canister 106 at a plurality of circumferentially spaced locations. A rotor member 114 of magnetically soft material is located in the internal cavity 108 and has an outer peripheral surface 116 engageable with the inner peripheral surface 110 of the internal cavity 108.

Pacemaker circuitry diagrammatically depicted at 118 is operable for sequentially energizing the plurality of electromagnets 112 to attract the rotor member 114 and force the rotor member to roll about the internal cavity 108 engaged with the inner peripheral surface 110. As in the previous embodiments, the rotor member 114, by its movement, produces vibrations which are imparted to the casing 22 of the organ stimulating system. Each of the electromagnets 112 includes a core member 120 mounted on the canister 106 and an electrically conductive coil 122 encircling the core member. The energizing expedients for the electromagnets include a source of electrical current provided by the pacemaker circuitry 118 and a plurality of signal generators 124, 126, 128, 130, each being associated with a different one of the electromagnets 112 for applying a periodic current to the associated one of the electromagnets.

As seen in the graph of FIG. 14, each of the electromagnets 112 is sequentially energized by voltage pulses 132, 134, 136, 138, respectively, which would typically be DC although AC bursts could be substituted.

Another variation of the annunciator 104 is illustrated in FIG. 15 and identified by reference numeral 104A. Because of the high orbital rates, it may be advantageous to use a series of magnetic circuits with air gaps on the cavity and a magnetically soft cylinder or ball. To this end, a plurality of electromagnets 140 are so arranged in an encircling configuration that together they define an internal cavity 142 having an inner peripheral surface 144. Each electromagnet 140 includes a core member 146 and an electrically conductive coil 148 encircling the core member. A rotor member 150 of magnetically soft material is located in the internal cavity 142 and has an outer peripheral surface 152 engageable with the inner peripheral surface 144 of the internal cavity. In all other respects as well, this embodiment is generally similar to the FIG. 13 embodiment. Furthermore, the FIG. 13 and 15 embodiments may each employ any or all of the constructions earlier described with respect to the other embodiments of the invention.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An annunciator for an organ stimulating system encapsulated within a casing and implantable in the body of a person comprising:

a canister mounted on the casing of the organ stimulating system, said canister having a cylindrical internal cavity with a longitudinal axis, an inner peripheral surface, an inside diameter, and opposed inner terminal surfaces;

a first electrically conductive coil encircling said canister and lying in a first plane;

a second electrically conductive coil encircling said canister and lying in a second plane transverse to the plane of said first conductive coil and intersecting said first electrically conductive coil along the longitudinal axis of the internal cavity of said canister;

a cylindrical permanent magnetic roller rotatable about a longitudinally extending roller axis having an outer peripheral surface engageable with said inner peripheral surface of said canister and being freely rotatable within the internal cavity thereof, said permanent magnetic roller being magnetized at right angles to the roller axis producing a permanent magnetic field; and means for sequentially energizing said first and second coils to produce a rotating magnetic field interacting with said permanent magnetic field of said magnetic roller to thereby cause said magnetic roller to roll about the internal cavity of said canister engaged with said inner peripheral surface, said permanent magnetic roller, by its movement, producing vibrations which are imparted to the casing of the organ stimulating system.

2. The annunciator for an organ stimulating system, as set forth in claim 1, wherein the vibrations imparted to the casing of the organ stimulating system exhibit a frequency exceeding both the rate of rotation of said magnetic roller about said roller axis and the rate of the sequential energization of said first and second coils.

3. The annunciator for an organ stimulating system, as set forth in claim 1, wherein said second conductive coil lies in a plane perpendicular to that of said first conductive coil.

4. The annunciator for an organ stimulating system, as set forth in claim 1:

wherein said permanent magnetic roller has a center of gravity;

wherein the rolling motion of said permanent magnetic roller about the internal cavity of said canister on said inner peripheral surface results in a movement of said center of gravity in an orbit which produces the vibrations which are imparted to the casing of the organ stimulating system; and wherein the orbital frequency, $\Omega$, of said center of gravity of said permanent magnetic roller is $\omega \cdot d/(D-d)$;

where $\omega$=rate of rotation of said roller;

where d=diameter of said roller; and where D=inner diameter of the cavity of said canister.

5. The annunciator for an organ stimulating system, as set forth in claim 1, wherein said energizing means includes:

a source of electrical current;

a first signal generator for applying a periodic current to said first electrically conductive coil; and a second signal generator for applying a periodic current to said second electrically conductive coil.

6. The annunciator for an organ stimulating system, as set forth in claim 1, wherein at least one of said outer peripheral surface of said permanent magnetic roller and said inner peripheral surface of said canister is roughened for optimum traction of said permanent magnetic roller on said inner peripheral surface.

7. The annunciator for an organ stimulating system, as set forth in claim 1, including a plurality of non-magnetic mini-balls within the internal cavity of said canister and interposed between said permanent magnetic roller and said inner terminal surfaces for minimizing friction therebetween.

8. The annunciator for an organ stimulating system, as set forth in claim 1, including wherein at least one of said outer peripheral surface of said permanent magnetic roller and said inner peripheral surface of said canister is ridged for producing vibrations as said permanent magnetic roller rolls along said inner peripheral surface.

9. A method of alerting a patient having an implanted organ stimulating system upon the occurrence of a predetermined event relating to the system comprising the steps of:

(a) mounting on the casing of the organ stimulating system a canister having a cylindrical internal cavity with a longitudinal axis, an inner peripheral surface, and opposed inner terminal surfaces;

(b) providing a magnetic cylindrical roller having a longitudinally extending roller axis and an outer peripheral surface in engagement with the inner peripheral surface of the canister and being freely rotatable within the internal cavity thereof, the magnetic roller being magnetized at right angles to the roller axis producing a permanent magnetic field;

(c) cyclically energizing a first electrically conductive coil encircling the canister and lying in a first plane to create a first electrical field;

(d) cyclically energizing a second electrically conductive coil encircling the canister and lying in a second plane transverse to the plane of the first conductive coil to create a second electrical field;

(e) consecutively performing steps (c) and (d) to cause an interaction between each of the first and second electrical fields and the magnetic field thereby imparting rolling movement to said magnetic roller along the inner peripheral surface within the internal cavity and producing vibrations; and (f) imparting the vibrations produced in step (e) to the casing of the organ stimulating system.

10. An annunciator for an organ stimulating system encapsulated within a casing and implantable in the body of a person comprising:

a canister mounted on the casing for the organ stimulating system, said canister having a spherical shaped internal cavity with an inner peripheral surface;

a first electrically conductive coil encircling said canister and lying in a first plane;

a second electrically conductive coil encircling said canister and lying in a second plane transverse to the plane of said first conductive coil;

said first and second electrically conductive coils intersecting at the center of the spherical shaped internal cavity of the canister;

a permanent magnetic ball having a diameter and an outer peripheral surface engageable with said inner peripheral surface of said canister and being freely rotatable within the internal cavity thereof, said permanent magnetic ball being magnetized along said diameter of said permanent magnetic ball and producing a magnetic field; and means for sequentially energizing said first and second coils to produce a rotating magnetic field interacting with said permanent magnetic field of said magnetic ball to thereby cause said magnetic ball to roll about the internal cavity of said canister engaged with said inner peripheral surface, said permanent magnetic ball, by its movement, producing vibrations which are imparted to the casing of the organ stimulating system.

11. An annunciator for an organ stimulating system encapsulated within a casing and implantable in the body of a person comprising:

a canister mounted on the casing of the organ stimulating system, said canister having an elongated internal cavity with a longitudinally extending major axis and a laterally extending minor axis, an inner peripheral surface, and opposed inner terminal surfaces;

a first electrically conductive coil encircling said canister and lying in a first plane;

a second electrically conductive coil encircling said canister and lying in a second plane transverse to the plane of said first conductive coil and intersecting said first electrically conductive coil, in one instance, along the longitudinal axis of the internal cavity of said canister and, in another instance, along the lateral axis of the internal cavity of said canister;

a permanent magnetic ball rotatable about a longitudinally extending roller axis having an outer peripheral surface engageable with said inner peripheral surface of said canister and being freely rotatable within the internal cavity thereof, said permanent magnetic ball being magnetized along a diameter of said ball producing a permanent magnetic field; and means for sequentially energizing said first and second coils to produce a rotating magnetic field interacting with said permanent magnetic field of said magnetic roller to thereby cause said magnetic roller to roll about the internal cavity of said canister engaged with said inner peripheral surface, said permanent magnetic roller, by its movement, producing vibrations which are imparted to the casing of the organ stimulating system.

12. An annunciator for an organ stimulating system encapsulated within a casing and implantable in the body of a person comprising:

a cylindrical permanent magnetic roller rotatable about a longitudinally extending roller axis having an outer peripheral surface and being magnetized at right angles to the roller axis producing a permanent magnetic field;

a first electrically conductive coil encircling said permanent magnetic roller and lying in a first plane;

a second electrically conductive coil encircling said permanent magnetic roller and lying in a second plane transverse to the plane of said first conductive coil;

said first and second electrically conductive coils being mounted on the casing for the organ stimulating system and together defining a generally cylindrical internal cavity with a longitudinal axis, an inner peripheral surface, and opposed inner terminal surfaces, said first and second electrically conductive coils intersecting along the longitudinal axis of the internal cavity thereof;

said permanent magnetic roller being engageable with said inner peripheral surface and being freely rotatable within the internal cavity thereof;

means for sequentially energizing said first and second coils to produce a rotating magnetic field interacting with said permanent magnetic field of said magnetic roller to thereby cause said magnetic roller to roll about the internal cavity engaged with said inner peripheral surface, said permanent magnetic roller, by its movement, producing vibrations which are imparted to the casing of the organ stimulating system.

13. The annunciator for an organ stimulating system, as set forth in claim 12, wherein the vibrations imparted to the casing of the organ stimulating system exhibit a frequency exceeding both the rate of rotation of said magnetic roller about said roller axis and the rate of the sequential energization of said first and second coils.

14. The annunciator for an organ stimulating system, as set forth in claim 12, including a plastic sheath encapsulating said first and second electrically conductive coils.

15. The annunciator for an organ stimulating system, as set forth in claim 14, including an iron housing surrounding said plastic sheath.

16. The annunciator for an organ stimulating system, as set forth in claim 12, wherein said second conductive coil lies in a plane perpendicular to that of said first conductive coil.

17. The annunciator for an organ stimulating system, as set forth in claim 12:

wherein said permanent magnetic roller has a center of gravity;

wherein the rolling motion of said permanent magnetic roller about the internal cavity of said canister on said inner peripheral surface results in a movement of said center of gravity in an orbit which produces the vibrations which are imparted to the casing of the organ stimulating system; and wherein the orbital frequency, $\Omega$, of said center of gravity of said permanent magnetic roller is $\omega \cdot d/(D-d)$, where $\omega$=rate of rotation of said roller;

where d=diameter of said roller; and where D=inner diameter of the cavity of said canister.

18. An annunciator for an organ stimulating system encapsulated within a casing and implantable in the body of a person comprising:

a plurality of electromagnets so arranged as to together define an internal cavity having a longitudinal axis and an inner peripheral surface;

a rotor member of magnetically soft material located in the internal cavity and having an outer peripheral surface engageable with said inner peripheral surface of the internal cavity; and means for sequentially energizing said plurality of electromagnets to attract said rotor member and force said rotor member to roll about the internal cavity engaged with said inner peripheral surface, said rotor member, by its movement, producing vibrations which are imparted to the casing of the organ stimulating system;

wherein said energizing means includes:

a source of electrical current; and a plurality of signal generators, each of said signal generators being associated with a different one of said electromagnets for applying a periodic current to an associated one of said electromagnets.

19. The annunciator for an organ stimulating system, as set forth in claim 18:

wherein said rotor member has a center of gravity;

wherein the rolling motion of said rotor member about the internal cavity on said inner peripheral surface results in a movement of said center of gravity in an orbit which produces the vibrations which are imparted to the casing of the organ stimulating system; and wherein the orbital frequency, $\Omega$, of said center of gravity of said permanent magnetic rotor member is $\omega \cdot d/(D-d)$;

where $\omega$=rate of rotation of said rotor member;

where d=diameter of said rotor member; and where D=inner diameter of the internal cavity.

20. The annunciator for an organ stimulating system, as set forth in claim 18, wherein each of said electromagnets includes a core member and an electrically conductive coil encircling said core member.

21. The annunciator for an organ stimulating system, as set forth in claim 18, wherein at least one of said outer peripheral surface of said rotor member and said inner peripheral surface of the internal cavity is ridged for producing vibrations as said rotor member rolls along said inner peripheral surface.

22. The annunciator for an organ stimulating system, as set forth in claim 18:

wherein said inner peripheral surface of the internal cavity is cylindrical; and wherein said rotor member is cylindrical and is rotatable about a longitudinally extending rotor axis.

23. The annunciator for an organ stimulating system, as set forth in claim 18:

wherein said inner peripheral surface of the internal cavity is spherical or ellipsoidal; and wherein said rotor member is a sphere having an outer peripheral surface engageable with said inner peripheral surface of the internal cavity and is freely rotatable within the internal cavity thereof.

24. An annunciator for an organ stimulating system encapsulated within a casing and implantable in the body of a person comprising:

a canister mounted on the casing of the organ stimulating system, said canister having a cylindrical internal cavity with a longitudinal axis and an inner peripheral surface;

a plurality of electromagnets attached to said canister at a plurality of circumferentially spaced locations;

a rotor member of magnetically soft material located in the internal cavity and having an outer peripheral surface engageable with said inner peripheral surface of the internal cavity; and means for sequentially energizing said plurality of electromagnets to attract said rotor member and force said rotor member to roll about the internal cavity engaged with said inner peripheral surface, said rotor member, by its movement, producing vibrations which are imparted to the casing of the organ stimulating system.

25. The annunciator for an organ stimulating system, as set forth in claim 24:

wherein said rotor member has a center of gravity;

wherein the rolling motion of said rotor member about the internal cavity on said inner peripheral surface results in a movement of said center of gravity in an orbit which produces the vibrations which are imparted to the casing of the organ stimulating system; and wherein the orbital frequency, $\Omega$, of said center of gravity of said permanent magnetic rotor member is $\omega \cdot d/(D-d)$;

where $\omega$=rate of rotation of said rotor member;

where d=diameter of said rotor member; and where D=inner diameter of the cavity of said canister.

26. The annunciator for an organ stimulating system, as set forth in claim 24, wherein said energizing means includes:

a source of electrical current; and a plurality of signal generators, each of said signal generators being associated with a different one of said electromagnets for applying a periodic current to an associated one of said electromagnets.

27. The annunciator for an organ stimulating system, as set forth in claim 24, wherein at least one of said outer peripheral surface of said rotor member and said inner peripheral surface of the cavity is roughened for optimum traction of said rotor member on said inner peripheral surface.

28. The annunciator for an organ stimulating system, as set forth in claim 24:

wherein said inner peripheral surface of the internal cavity is cylindrical; and wherein said rotor member is cylindrical and is rotatable about a longitudinally extending rotor axis.

29. The annunciator for an organ stimulating system, as set forth in claim 24:

wherein said inner peripheral surface of the internal cavity is spherical or ellipsoidal; and wherein said rotor member is a sphere having a diameter and an outer peripheral surface engageable with said inner peripheral surface of the internal cavity and is freely rotatable within the internal cavity thereof.

30. The annunciator for an organ stimulating system, as set forth in claim 24, wherein each of said electromagnets includes a core member mounted on said canister and an electrically conductive coil encircling said core member.

31. A method of alerting a patient having an implanted organ stimulating system upon the occurrence of a predetermined event relating to the system comprising the steps of:

(a) mounting on the casing of the organ stimulating system a plurality of electromagnets so arranged as to together define an internal cavity having a longitudinal axis and an inner peripheral surface;

(b) providing a rotor member of magnetically soft material located in the internal cavity and having an outer peripheral surface in engagement with the inner peripheral surface of the internal cavity and being freely rotatable within the internal cavity; and (c) sequentially energizing the plurality of electromagnets to attract the rotor member and force the rotor member to roll about the internal cavity engaged with the inner peripheral surface, thereby producing vibrations which are imparted to the casing of the organ stimulating system.

* * * * *